United States Patent [19]

Namdaran et al.

[11] Patent Number: 5,403,901
[45] Date of Patent: Apr. 4, 1995

[54] FLEXIBLE, HIGH REFRACTIVE INDEX POLYMERS

[75] Inventors: Farhad H. Namdaran, Bellevue, Wash.; Albert R. LeBoeuf, Fort Worth, Tex.

[73] Assignee: Nestle S.A., Vevey, Switzerland

[21] Appl. No.: 157,789

[22] Filed: Nov. 24, 1993

Related U.S. Application Data

[63] Continuation of Ser. No. 76,378, Jun. 14, 1993, Pat. No. 5,290,892, which is a continuation of Ser. No. 837,796, Feb. 18, 1992, abandoned, which is a continuation-in-part of Ser. No. 609,863, Nov. 7, 1990, abandoned.

[51] Int. Cl.$^6$ .................................... C08F 226/06
[52] U.S. Cl. ........................... 526/259; 526/292.2; 526/292.3; 526/313; 526/296
[58] Field of Search .................. 526/259, 313, 323.2, 526/323, 323.1, 326, 328.5, 292.2, 292.3, 292.1, 292.5, 292.6, 294, 296, 307.5

[56] References Cited

U.S. PATENT DOCUMENTS

| | | | |
|---|---|---|---|
| 3,850,892 | 11/1974 | Shen et al. | 160/80.72 |
| 3,932,321 | 1/1976 | Maki . | |
| 4,036,814 | 7/1977 | Howes et al. . | |
| 4,304,895 | 12/1981 | Loshaek | 526/313 |
| 4,393,184 | 7/1983 | Tarumi et al. | 526/261 |
| 4,393,184 | 7/1983 | Tarumi | 526/292.1 |
| 4,518,756 | 5/1985 | Yoshida et al. | 526/313 |
| 4,528,311 | 7/1985 | Beard et al. | 524/91 |
| 4,704,006 | 11/1987 | Sakagami et al. | 350/409 |
| 4,761,438 | 8/1988 | Komiya et al. | 523/106 |
| 4,834,750 | 5/1989 | Gupta | 623/6 |

FOREIGN PATENT DOCUMENTS

| | | |
|---|---|---|
| 0273710 | 7/1988 | European Pat. Off. . |
| 59-136310-A | 1/1983 | Japan . |
| 60-202110-A | 3/1984 | Japan . |
| 136610 | 8/1984 | Japan . |
| 014202 | 1/1985 | Japan . |
| 098710 | 5/1986 | Japan . |
| 63109866-A | 10/1986 | Japan . |
| 055736 | 2/1990 | Japan . |
| 086712 | 4/1991 | Japan . |

OTHER PUBLICATIONS

WO86/04343 Jul. 1986.

*Primary Examiner*—Christopher Henderson
*Attorney, Agent, or Firm*—Sally Yeager; Patrick M. Ryan

[57] ABSTRACT

High refractive index copolymers comprised of monomers having the formula:

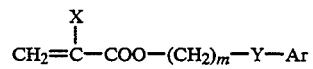

wherein
X is H or $CH_3$;
m is 0-10;
Y is nothing, O, S, or NR wherein R is H, $CH_3$, $C_nH_{2n+1}$ (n=1-10) iso $OC_3H_7$, $C_6H_5$, or $CH_2C_6H_5$;
Ar is an aromatic ring which is unsubstituted or substituted with H, $CH_3$, $C_2H_5$, n-$C_3H_7$, iso-$C_3H_7$, $OCH_3$, $C_6H_{11}$, Cl, Br, $C_6H_5$ or $CH_2C_6H_5$; and n is 1-5; and a cross linking monomer having a plurality of polymerizable ethylenically unsaturated groups are disclosed. Intraocular lenses made of the copolymers which can be inserted into an aphakic eye through a relatively small incision are also disclosed.

1 Claim, 2 Drawing Sheets

FLEXIBLE, HIGH REFRACTIVE INDEX POLYMERS

This is a continuation of U.S. Patent Application Ser. No. 08/076,378, filed Jun. 14, 1993, now U.S. Pat. No. 5,290,892, which is a continuation of Ser. No. 07/837,796, filed Feb. 18, 1992, now abandoned, which is a continuation in part of Ser. No. 07/609,863, filed on Nov. 7, 1990, now abandoned.

FIELD OF THE INVENTION

This invention relates to polymers and their use in ophthalmic lenses, particularly intraocular lenses that can be inserted through small incisions.

BACKGROUND OF THE INVENTION

In response to the development of cataractous lenses, it has become common to replace the lens with an intraocular lens (IOL) in a surgical procedure. In order to reduce the trauma to the eye in cataract surgery, it is desirable to keep the incision through which the surgical procedure is conducted as small as possible. With the development of phacoemulsification surgery, in which the lens is fragmented by ultrasonic vibrations and the fragments aspirated through a small cannula, it has become possible to remove a lens through an incision no larger than 2-3 millimeters. However, since an IOL is typically at least six millimeters in diameter, an incision at least that large has to be made to permit the insertion of the IOL. In order to permit the use of the desirable small incision technique, various flexible, distortable, and inflatable IOLs have been devised.

Juergens, U.S. Pat. No. 4,619,662, discloses a collapsible intraocular lens with a hollow interior which can be evacuated to cause the lens to collapse to a relatively small size. The collapsed lens can then be inserted into the eye through a relatively small incision. After insertion, the interior of the lens is filled with an elastomer to expand the lens to the proper shape and dimension.

Mazzocco, U.S. Pat. No. 4,573,998, discloses a deformable intraocular lens that can be rolled, folded, or stretched to fit through a relatively small incision. The deformable lens is inserted while it is held in its distorted configuration, then released inside the chamber of the eye, whereupon the elastic property of the lens causes it to resume its molded shape. As suitable materials for the deformable lens, Mazzocco discloses polyurethane elastomers, silicone elastomers, hydrogel polymer compounds, organic or synthetic gel compounds and combinations thereof.

Keates et al., U.S. Pat. No. 4,619,657, disclose a flexible intraocular lens holder made from a flexible inert polymer, such as silicone rubber, which contains pockets for receiving individual lenses which are small enough to fit through a relatively small incision. The lens holder is folded or rolled and inserted through a small incision and thereafter several of the small lenses are inserted through the incision and into the pockets in the lens holder to form a composite intraocular lens.

A number of these known methods of providing an intraocular lens which can be inserted through a small incision have suffered from the excessive complexity of inflatable lenses or composite lenses. The deformable intraocular lenses are simpler to manufacture and use; however, when they are made of materials hitherto employed, such as polyurethane elastomers and silicone elastomers, which have a relatively low refractive index, they must be relatively thick in order to provide a lens of the proper refractive power. The thicker the lens, the more difficult it is to deform or distort it into a shape which will fit through a small incision. Furthermore, the distortion required to force a thick lens through a small incision may exceed its elastic properties so that it breaks or will not recover its original shape when released within the eye. Therefore, lenses made from such materials are somewhat limited as to the minimum size to which they may be deformed.

Accordingly, there is a need for a material, with a relatively high refractive index, which can be used to form a flexible intraocular lens which can be simply rolled or folded into a configuration which will fit through a small incision.

SUMMARY OF THE INVENTION

This invention is directed to high refractive index polymers produced by copolymerization of monomers having the following structure:

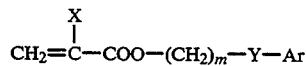

wherein:

X is H or $CH_3$;

m is 0-10;

Y is nothing, O, S, or NR wherein R is H, $CH_3$, $C_nH_{2n+1}$ (n=1-10) iso $OC_3H_7$, $C_6H_5$, or $CH_2C_6H_5$;

Ar is any aromatic ring which can be unsubstituted or substituted with H, $CH_3$, $C_2H_5$, n-$C_3H_7$, iso-$C_3H_7$, $OCH_3$, $C_6H_{11}$, Cl, Br, $C_6H_5$, or $CH_2C_6H_5$; and a cross-linking monomer having a plurality of polymerizable ethylenically unsaturated groups.

These polymers can be used to form intraocular lenses that have high refractive indexes, are flexible and transparent, can be inserted into the eye through a relatively small incision, and recover their original shape after having been inserted.

Further objects of the invention will be apparent from the description of the invention which follows.

DETAILED DESCRIPTION OF THE INVENTION AND PREFERRED EMBODIMENTS

Figure 1:
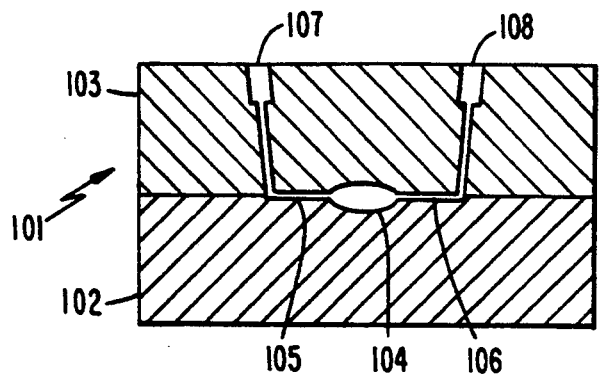
FIG. 1 shows a cross-section of a mold usable in preparing a flexible intraocular lens according to the invention.

The refractive power of a lens is a function of its shape and the refractive index of the material of which it is made. A lens made from a material having a higher refractive index can be thinner and provide the same refractive power as a lens made from a material having a relatively lower refractive index.

In intraocular lenses designed to be rolled or folded for insertion through a small incision, a lens of thinner cross section is inherently more flexible and can be rolled or folded to a smaller cross section. The flexible intraocular lenses of this invention, because of the high refractive index of the polymer from which they are molded, can be made thinner than a lens made from a polymer with a lower refractive index, such as a polyurethane, or silicone. Accordingly, the intraocular lenses of this invention are capable of being reduced to a smaller diameter than known flexible IOLs, and therefore permit the use of a smaller incision.

The polymers used in preparing the flexible intraocular lenses of the invention comprise copolymers, of monomers having the formula:

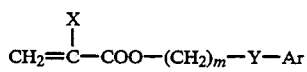

wherein:
X is H or $CH_3$;
m is 0–10;
Y is nothing, O, S, or NR wherein R is H, $CH_3$, $C_nH_{2n+1}$ (n=1–10) iso $OC_3H_7$, $C_6H_5$, or $CH_2C_6H_5$;
Ar is any aromatic ring, such as benzene, which can be unsubstituted or substituted with H, $CH_3$, $C_2H_5$, n-$C_3H_7$, iso-$C_3H_7$, $OCH_3$, $C_6H_{11}$, Cl, Br, $C_6H_5$ or $CH_2C_6H_5$; and
a cross-linking monomer having a plurality of polymerizable ethylenically unsaturated groups. The polymers have a glass transition temperature not greater than 37° C. and an elongation of at least 150%.

Suitable monomers include, but are not limited to: 2-ethylphenoxy methacrylate, 2-ethylphenoxy acrylate, 2-ethylthiophenyl methacrylate, 2-ethylthiophenyl acrylate, 2-ethylaminophenyl methacrylate, phenyl methacrylate, benzyl methacrylate, 2-phenylethyl methacrylate, 3-phenylpropyl methacrylate, 4-phenylbutyl methacrylate, 4-methylphenyl methacrylate, 4-methylbenzyl methacrylate, 2-2-methylphenylethyl methacrylate, 2-3-methylphenylethyl methacrylate, 2-4-methylphenylethyl methacrylate, 2-(4-propylphenyl)ethyl methacrylate, 2-(4-(1-methylethyl)phenyl)ethyl methacrylate, 2-(4-methoxyphenyl)ethyl methacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate), 2-(4-phenylphenyl)ethyl methacrylate), 2-(4-benzylphenyl)ethyl methacrylate, and the like, including the corresponding methacrylates and acrylates.

The copolymerizable cross-linking agent used in the polymers of this invention may be any terminally ethylenically unsaturated compound having more than one unsaturated group. Suitable cross-linking agents include, for example: ethylene glycol dimethacrylate, diethylene glycol dimethacrylate, allyl methacrylate, 1,3-propanediol dimethacrylate, allyl methacrylate, 1,6-hexanediol dimethacrylate, 1,4-butanediol dimethacrylate, and the like. A preferred cross-linking agent is 1,4-butanediol diacrylate (BDDA).

It will be understood by those skilled in the art, that among polymers of acrylic esters, those made from acrylate ester monomers tend to have lower glass transition temperatures and to be more flexible than polymers of methacrylate esters. Accordingly, the aryl acrylate/methacrylate copolymers used in the IOL's of this invention will generally comprise a greater mole percent of acrylate ester residues than of methacrylate ester residues. It is preferred that the aryl acrylate monomers constitute from about 60 mole percent to about 95 mole percent of the polymer, while the aryl methacrylate monomers constitute from about 5 mole percent to about 40 mole percent of the polymer. Most preferred is a polymer comprising about 60–70 mole percent 2-phenylethyl acrylate (PEA) wherein, in the structure set forth above X is H, m is 2, and Ar is benzene; and about 30–40 mole percent 2-phenylethyl methacrylate (PEMA), wherein, in the structure set forth above X is $CH_3$, m is 2, and Ar is benzene.

The proportions of the monomers should be chosen to produce a polymer having a glass transition temperature not greater than about 37° C., which is normal human body temperature. Polymers having glass transition temperatures higher than 37° C. are not suitable; such lenses could only be rolled or folded at temperatures above 37° C. and would not unroll or unfold at normal body temperature. It is preferred to use polymers having a glass transition temperature somewhat below normal body temperature and no greater than normal room temperature, e.g., about 20° C.–25° C., in order that the lenses can be rolled or folded conveniently at room temperature.

The lenses must exhibit sufficient strength to allow them to be folded without fracturing. Polymers exhibiting an elongation of at least 150% are preferred. Most preferably, the polymers exhibit an elongation of at least 200%. Lenses made from polymers which break at less than 150% elongation may not endure the distortion which necessarily occurs when they are rolled or folded to a dimension small enough to pass through a small incision.

The polymers of this invention are prepared by generally conventional polymerization methods. A mixture of the liquid monomers in the desired proportions together with a conventional thermal free-radical initiator is prepared. The mixture can then be introduced into a mold of suitable shape to form the lens and haptic in one integral unit, and the polymerization carried out by gentle heating to activate the initiator. Typical thermal free radical initiators include peroxides, such as benzophenone peroxide, peroxycarbonates, such as bis-(4-t-butulcyclohexyl) peroxydicarbonate, azonitriles, such as azobisisobytyronitrile, and the like. A preferred initiator is bis-(4-t-butylcyclohexyl) peroxydicarbonate (PERK). Alternatively, the monomers can be photopolymerized by using a mold which is transparent to actinic radiation of a wavelength capable of initiating polymerization of these acrylic monomers by itself. Conventional photoinitiator compounds, e.g., a benzophenone-type photoinitiator, can also be introduced to facilitate the polymerization. Photosensitizers can be introduced as well to permit the use of longer wavelengths; however, in preparing a polymer which is intended for long residence within the eye, it is generally preferable to keep the number of ingredients in the polymer to a minimum to avoid the presence of materials which might leach from the lens into the interior of the eye.

An ultra-violet absorbing material can also be included in the polymeric lenses of this invention in order that the lenses may have an ultraviolet absorbance approximately that of the natural lens of the eye. The ultraviolet absorbing material can be any compound which absorbs ultraviolet light, i.e., light having a wavelength shorter than about 400 nm, but does not absorb any substantial amount of visible light. The ultraviolet absorbing compound is incorporated into the monomer mixture and is entrapped in the polymer matrix when the monomer mixture is polymerized. Suitable ultraviolet absorbing compounds include substituted benzophenones, such as 2-hydroxybenzophenone, and 2-(2-hydroxyphenyl)benzotriazoles. It is preferred to use an ultraviolet absorbing compound which is co-polymerizable with the monomers and is thereby covalently bound to the polymer matrix. In this way possible leaching of the ultraviolet absorbing compound out of the lens and into the interior of the eye is minimized. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. The most preferred ultraviolet absorbing compound is 2-(3'-methallyl-2'-hydroxy-5'methyl phenyl) benzotriazole.

IOLs constructed of the disclosed polymers can be of any design capable of being rolled or folded into a small cross section that can fit through a relatively smaller incision. For example, the IOLs can be of what is known as a one piece or multipiece design. Typically, an IOL comprises an optic and at least one haptic. The optic is that portion which serves as the lens and the haptics are attached to the optic and are like arms which hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

Figure 8:
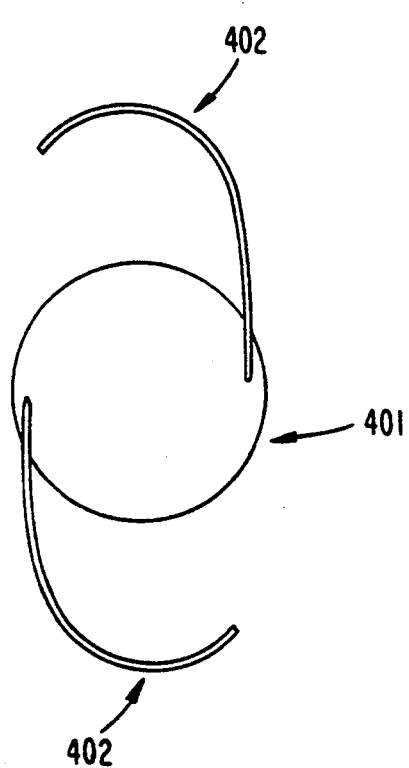
FIG. 8 shows a multipiece intraocular lens.

The preferred IOL of the present invention is shown in FIG. 8 and is a multi-piece lens wherein the optic 401 comprises about 65 wt. % PEA, 30 wt. % PEMA, 3.2 wt. % BDDA and 1.8 wt. % 2-(3'methallyl-2'-hydroxy-5'-methylphenyl) benzotriazole and the haptics 402 are made of polymethyl methacrylate (PMMA). Such a lens can be made by first molding the optic using the monomers and U.V. absorbing materials as described herein.

Figure 9:
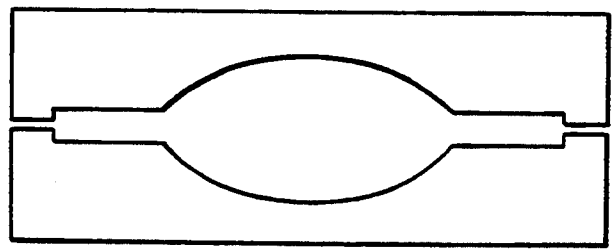
FIG. 9 shows a cross section of a mold for making intraocular lenses.
Figure 10:
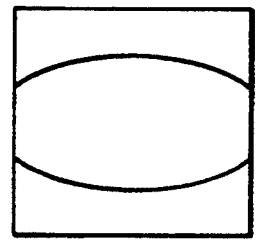
FIG. 10 shows a mold containing an optic cut to the desired optic diameter.

The molding and drilling operation are easily carried out if the optic is molded between two polypropylene mold halves as shown in FIG. 9. The mold containing the cured optic material is then placed on a lathe and the desired optic diameter is lathe cut. The resultant optic/mold sandwich is shown in FIG. 10. This may be easily mounted to carry out any drilling operations prior to removing the mold halves. Both the lathing and drilling operations may be facilitated by cooling the mold/optic in a freezer to less than 10° C. and preferably less than 0° C. prior to each of these operations.

Figure 5:
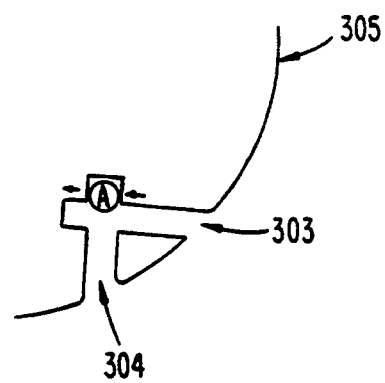
FIGS. 5-7 show a portion of the optic portion of an intraocular lens with holes for attaching haptics.
Figure 6:
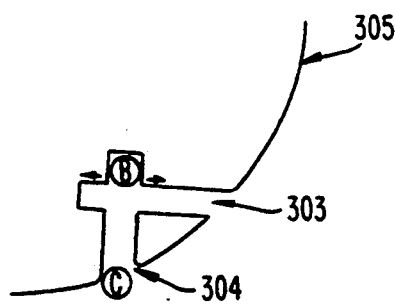
Figure 7:
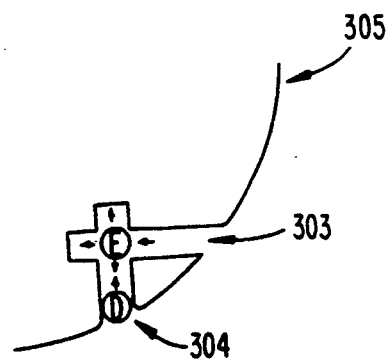

In order to attach a haptic 402 to the optic 401, two holes are drilled into the side of the lens (which is exposed as shown in the optic/mold sandwich of FIG. 10) as shown in FIGS. 5, 6, and 7. The hole 303 carries the haptic. Hole 304 carries the haptic anchor. In order to attach the haptic to the optic 305, a PMMA haptic (blue core VS-100) is inserted fully into hole 303. A laser beam (450–520 nm) which will produce a spot diameter of 100 microns is then aimed at the intersection of the two holes, point E, FIG. 7. A PMMA haptic (blue core VS-100) anchor strand is then inserted into hole 304 to the point that the optic 305 distorts, FIG. 1. The laser beam is then aimed and fired at point A, FIG. 1. While firing, the haptic anchor strand is moved back and forth in the direction of the arrows in FIG. 1 until the optic relaxes, FIG. 6. This process is repeated until the back of anchor hole 304 is full of material (PMMA). The laser is then aimed at point C and fired until the haptic anchor strand is severed. The laser is then aimed at point D and fired causing the cut end of the haptic anchor strand to draw into the hole 304. The laser is then aimed at point E and fired, moving in all directions as shown by the arrows until the weld is smooth. This procedure is repeated until the desired number of haptics, usually two, are attached to the optic 305. Blue polypropylene haptics can also be used rather than PMMA haptics.

The invention will be further illustrated by the following examples which are intended to be illustrative, but not limiting.

EXAMPLE 1

These examples illustrate the preparation of polymers and flexible intraocular lenses made of such polymers according to this invention.

A mixture of 90 mole percent 2-phenylethyl acrylate (PEA), 5 mole percent 2-phenylethyl methacrylate (PEMA), 5 mole percent 1-6 hexanediol dimethacrylate (HDDMA), and 0.1 percent by weight of bis-(4-t-butyl-cyclohexyl) peroxydicarbonate was degassed and transferred into two molds: (1) an IOL mold of the type illustrated in FIG. 1 and (2) a film mold made of two glass plates with one layer of a polyethylene terephthalate film on each facing side, with the plates being separated by a silicone gasket of 0.8 mm thickness. Both molds were designed so that there would be no differential pressure buildup between the inside and the outside of the mold during the polymerization. The mold 101 illustrated in FIG. 1 comprises a bottom portion 102 and a top portion 103, which contain recesses which cooperate when the mold is assembled to form a cavity having an optic forming portion 104 and haptic forming portions 105 and 106. The top portion 103 of the mold is provided with a filling port 108 and a vent 107. The mold was completely filled by injecting the mixture, e.g., by means of a syringe, into filling port 108 until the mold was filled and excess monomer mixture was discharged through vent 107.

The filled molds were heated in an inert environment, for 15 hours at 50° C. At the end of the polymerization period, the molds were opened and the cured intraocular lens and sheet of polymer were removed. The intraocular lens was found to be soft, foldable, and of high refractive index (approximately 1.55) with a glass transition temperature of approximately 12° C.

Additional lenses were made using the above procedure but varying the proportions of the ingredients. The formulations and physical properties of the lenses made from the polymers are summarized in Table 1, Examples 1–10.

TABLE 1

| Example | Monomer Composition* (Mole %) | | | | Properties** | | | |
|---|---|---|---|---|---|---|---|---|
| | PEA | PEMA | HDDMA | BDDA | Tg (°C.) | Elongation (%) | $N^{20}_D$ | Tan |
| 1 | 90 | 5 | 5 | | 12 | — | 1.5520 | 0.08 |
| 2 | 89.5 | 10 | 0.5 | | 10 | 490 | 1.5512 | 0.16 |
| 3 | 89.0 | 10 | 1.0 | | 11 | 330 | 1.5499 | 0.32 |
| 4 | 88.5 | 10 | 1.5 | | 10 | 200 | 1.5500 | 0.16 |
| 5 | 88.0 | 10 | 2.0 | | 10 | 220 | 1.5572 | 0.10 |
| 6 | 79.5 | 20 | 0.5 | | 13 | 500 | 1.5520 | 0.45 |
| 7 | 79.0 | 20 | 1.0 | | 11 | 300 | 1.5536 | 0.23 |
| 8 | 78.5 | 20 | 1.5 | | 11 | 220 | 1.5518 | 0.29 |
| 9 | 78.0 | 20 | 2.0 | | 15 | 230 | 1.5501 | 0.25 |
| 10 | 70.0 | 30.0 | | 3.0 | 20 | 200 | 1.5584 | 0.25 |

*PEA — Phenylethyl acrylate
PEMA — Phenylethyl methacrylate
HDDMA — 1-6 Hexanediol dimethacrylate
BDDA — 1-4 Butanediol diacrylate
**Tg — Glass Transition Temperature
Elongation - Ultimate Elongation at 20° C.
$N^{20}$ — Refractive Index at 20° C.
Tan — Ratio of loss modulus over storage modulus at 37° C.

The glass transition temperature (Tg) was measured by differential thermal analysis using conventional equipment. The ultimate elongation was measured at 20° C. by means of a Mini-Mat elongation instrument manufactured by Polymer Labs, Inc., wherein coupons cut from the 0.8 mm thick sheets where clamped in opposing jaws which were drawn apart until the samples fractured. The refractive index at 20° C. was measured with an Abbe refractometer. The ratio of loss modulus over storage modulus (Tan) at 37° C. was measured with a Dynamic Mechanical Thermal Analyzer manufactured by Polymer Labs, Inc., wherein a sample of the 0.8 mm thick sheet was vibrated and the ratio of restoring force to exciting force was determined.

Figure 2:
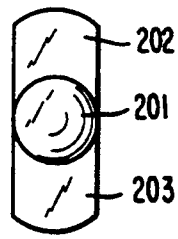
FIG. 2 shows a front view of an intraocular lens of the invention.
Figure 3:
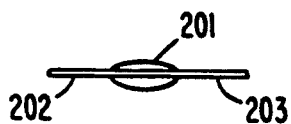
FIG. 3 shows a side view of an intraocular lens of the invention in its extended configuration.
Figure 4:
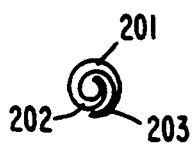
FIG. 4 shows a side view of an intraocular lens of the invention in a rolled configuration.

The lenses prepared using the mold 101 of FIG. 1 had a shape as illustrated by FIGS. 2 and 3 comprised of a central optic 201 with integrally molded haptics 202 and 203. The lenses were rolled into small, generally cylindrical shapes as shown in FIG. 4 having a diameter small enough to be inserted through an incision about 3 mm in length. The rolled lenses were passed through a small aperture, such as a cannula, and observed to recover their molded shape after being released from the confinement of the cannula.

The results of these experiments demonstrate that the lenses of this invention can be inserted into the eye after extracapsular removal of cataractous lens, e.g., by phacoemulsification through an incision of about 3 mm and will restore themselves within the eye to the proper shape for replacing the patient's natural lens.

EXAMPLE 2

The following polymers were made according to the procedure described below.

TABLE 2

| | 1 | 2 | 3 | 4 | 5 | 6 | 7 | 8 | 9 |
|---|---|---|---|---|---|---|---|---|---|
| PEMA | 30 | 15 | 15 | 17 | 15 | 30 | 30 | 30 | 30 |
| PEA | 65 | 80 | 80 | 80 | 80 | 65 | — | — | 65 |
| PPA | — | — | — | — | — | — | 65 | — | — |
| POEA | — | — | — | — | — | — | — | 65 | — |
| UVC | 1.8 | .5 | .5 | .5 | .5 | .5 | .5 | .5 | — |
| BDDA | 3.2 | 3.2 | — | — | — | — | 3.2 | 3.2 | 3.2 |
| DDDA | — | — | 3.2 | — | — | — | — | — | — |
| PE400DA | — | — | — | 3.2 | — | — | — | — | — |
| PE1000DRA | — | — | — | — | 3.2 | 10 | — | — | — |
| BZP | 1 | 1 | 1 | 1 | 1 | 1 | 1 | 1 | 1 |
| INSTRON (tensile tester) | | | | | | | | | |
| modulus | 125 | 111 | 96 | 109 | 78 | 64 | 129 | | 162 |
| % elong | 285 | 158 | 228 | 355 | 432 | 331 | 146 | | 223 |
| tensile | 344 | 173 | 154 | 139 | 105 | 215 | 137 | | 315 |
| Refractive Index | 1.556 | 1.554 | 1.553 | 553 | | | | | |
| Tg | 17 | 11 | 10 | 7 | 7.9 | | 4.5 | | |

Material Code
PEA 2-Phenylethyl Acrylate
PEMA 3-Phenylethyl Methacrylate
PPA 3-Phenylpropyl Acrylate
POEA 2-Phenoxyethyl Acrylate (Polysciences, caustic washed)
UVC o-MTP UV-Chromophore (2-(3'-Methallyl-2'-hydroxy-5'methyl phenyl) benzotriazole
BDDA Butanediol Diacrylate X-Linker
DDDA 1,10 Decandediol Diacrylate X-Linker
PEG400DA Polyethyleneglycol 400 Diacrylate X-Linker
PEG1000DMA Polyethyleneglycol 1000 Dimethacrylate X-Linker
BZP Benzoyl Peroxide

PROCEDURE

All samples were evaluated in the form of 1 mm thick sheet castings. A mold was formed of two glass plates separated by a 1 mm thick teflon spacer having a slit for the insertion of a hypodermic needle to which a 50 cc syringe containing the monomer formulation under investigation was attached. Following the clamping together of the casting mold with spring clamps, the mold was filled with the formulation until all bubbles were eliminated from the casting. The filled fixture was then placed into an air circulating oven and cured for 16 to 18 hours at 65° C.+3 hrs at 100° C. All polymers were flexible and suitable for use in an IOL.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. A copolymer comprising 2-phenylethyl acrylate at a concentration of about 65 wt. %; 2-phenylethyl methacrylate at a concentration of about 30 wt. %; 1,4-butanediol diacrylate at a concentration of about 3.2 wt. % and 2-(-3'-methallyl-2'-hydroxy-5'-methylphenyl)-benzotriazole at a concentration of about 1.8 wt. %.

* * * * *

UNITED STATES PATENT AND TRADEMARK OFFICE
CERTIFICATE OF CORRECTION

PATENT NO.   : 5,403,901

DATED        : April 4, 1995

INVENTOR(S)  : Namdaran et al.

It is certified that error appears in the above-identified patent and that said Letters Patent is hereby corrected as shown below:

Col. 8, TABLE 2, "Material Code" Legend, definition of "PEMA": "3-Phenylethyl" should read --2-Phenylethyl--.

Signed and Sealed this

Twelfth Day of December, 1995

Attest:

Attesting Officer

BRUCE LEHMAN

Commissioner of Patents and Trademarks